United States Patent [19]

Rosenfeld et al.

[11] Patent Number: 4,755,675
[45] Date of Patent: Jul. 5, 1988

[54] GAS ANALYZER AND A SOURCE OF IR RADIATION THEREFOR

[75] Inventors: Elieser Z. Rosenfeld; Hanan Boasson, both of Jerusalem, Israel

[73] Assignee: Irad Technologies Ltd., Jerusalem, Israel

[21] Appl. No.: 946,876

[22] Filed: Dec. 29, 1986

[30] Foreign Application Priority Data

Jan. 1, 1986 [IL] Israel ........................................ 77494

[51] Int. Cl.[4] .............................................. G01N 21/35
[52] U.S. Cl. ...................................... 250/343; 250/345; 250/493.1
[58] Field of Search ................. 250/504 R, 493.1, 343, 250/344, 345, 346; 313/112, 643, 638; 372/4, 55, 70

[56] References Cited

U.S. PATENT DOCUMENTS

| | | | |
|---|---|---|---|
| 3,614,653 | 10/1971 | Javan | 372/70 |
| 4,005,330 | 1/1977 | Glascock, Jr. et al. | 313/491 |
| 4,274,063 | 6/1981 | Javan | 372/55 |
| 4,437,005 | 3/1984 | Ophoff et al. | 250/343 |
| 4,468,561 | 8/1984 | Speeter | 250/343 |
| 4,596,931 | 6/1986 | Ehnholm et al. | 250/343 |
| 4,648,396 | 3/1987 | Raemer | 250/343 |
| 4,652,790 | 3/1987 | Wood | 313/112 |

Primary Examiner—Carolyn E. Fields
Assistant Examiner—John A. Miller
Attorney, Agent, or Firm—Scully, Scott, Murphy & Presser

[57] ABSTRACT

A source of IR radiation for use with a gas analyzer including a sealed-off enclosure containing at least one molecular, IR-active gas which, upon excitation, is capable of emitting IR-radiation of a known, discrete spectral distribution. The excitation is effected by electrical discharges taking place in a limited portion only of the sealed-off enclosure, the rest of the enclosure serving as reservoir of the gas. The electrodes producing the discharges are disposed outside of the enclosure. A gas analyzer incorporating the source is also described.

12 Claims, 2 Drawing Sheets

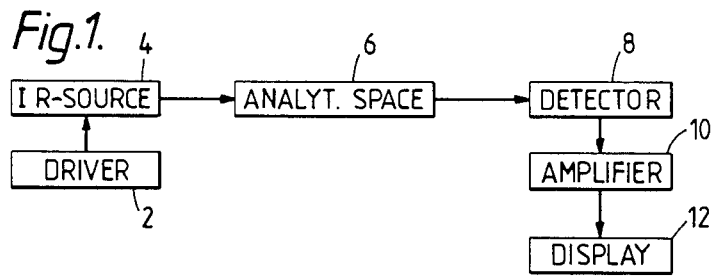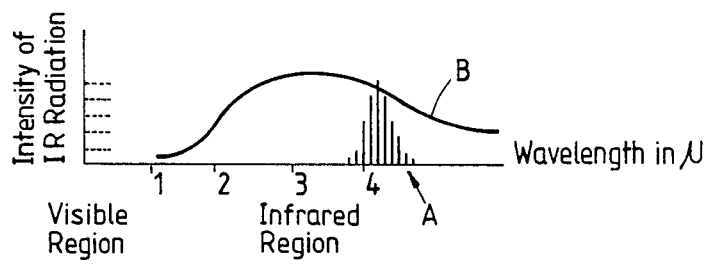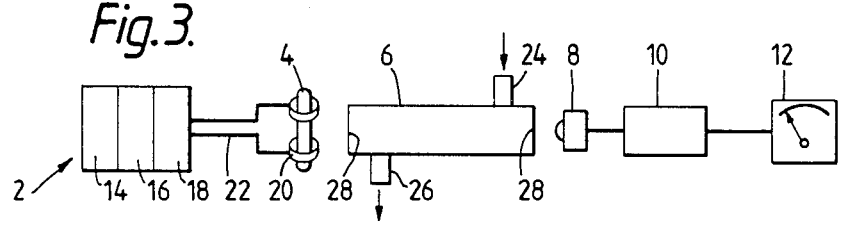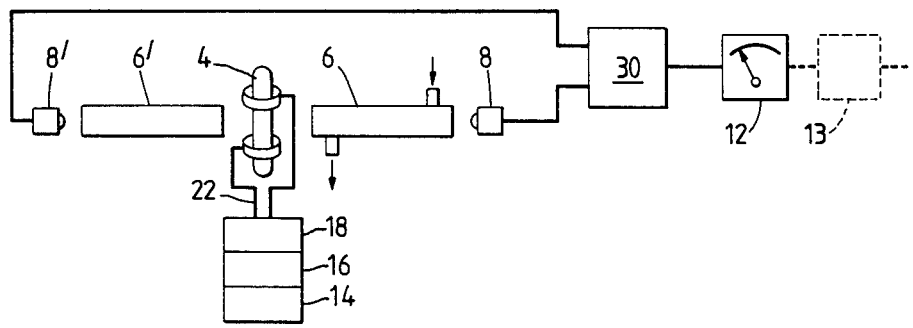

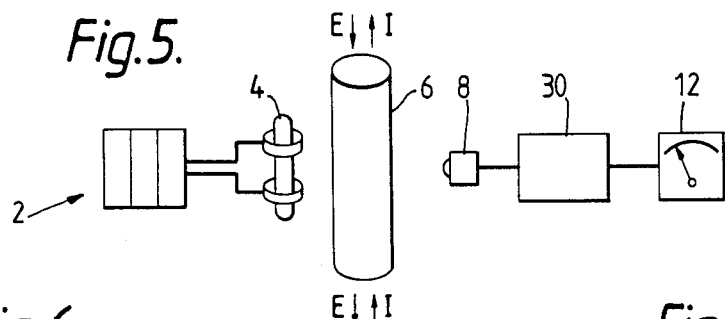
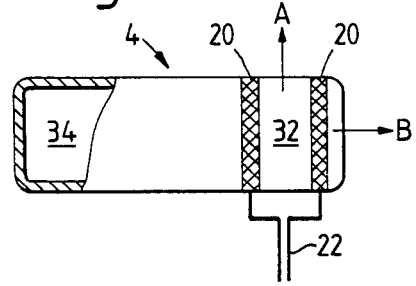
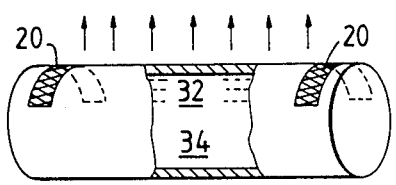
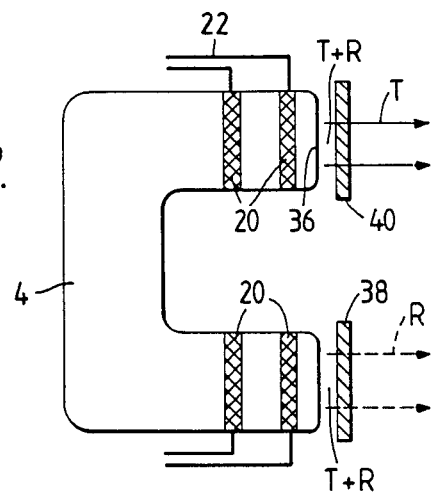
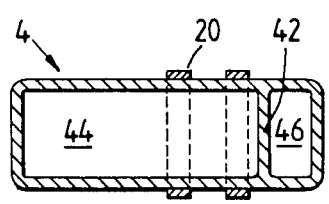

GAS ANALYZER AND A SOURCE OF IR RADIATION THEREFOR

The present invention relates to an infrared gas analyzer, that is, a device using infrared radiation to determine, in a gas sample, the presence and concentration of a selected gas.

Infrared gas analysis is based on the absorption, by infrared-active gas molecules undergoing transitions between roto-vibrational levels, of radiation in this particular region of the spectrum. Each of these gases has its own very specific infrared absorption band, which can be regarded as its infrared "signature". If the gas to be analyzed is placed between an infrared source and a detector, its concentration can be determined by measuring the absorption at wavelengths corresponding to this "signature".

Gas analyzers based on the IR-absorption principle are well known in the prior art, and while they differ in their respective designs, they have several features in common, the most important one of which is the IR-source which, with almost all of them is a "black body" (BB) thermal radiator in the form of a solid heated to incandescence. Such radiators produce a continuous spectrum covering the entire range from the far IR (about $20\mu$) into the visible region (about $0.5\mu$) and are used generally in conjunction with band pass filters which reduce this extensive spectral range to that where most of the "signature" band lines of the target gas are located. In order to detect the amount of absorption, most BB-source equipped instruments incorporate also a mechanical "chopper" to modulate the radiation reaching the detector, as the source itself (the incandescent solid) cannot be modulated directly, at a rate fast enough for convenient electronic processing, because of its high thermal capacity and, consequently, thermal inertia. The power consumption of a gas analyzer incorporating a BB-source is relatively high (up to 50 W) and, considering the added complexities introduced by the need for filtering, mechanical "chopping" of the radiation and the elaborate associated electronic circuitry, so is their price. With even the large, stationary, laboratory type of these instruments occasionally showing a less than satisfactory selectivity and sensitivity, portability has in the past been achieved only at the expense of further reduction of these qualities.

IR-sources other than BB-radiators were disclosed by Webley (U.K. No. 1591709) and Javan (U.S. Pat. No. 4,274,063); both of whom proposed IR-sources in the form of gas discharge tubes. Webley, however, explicitly stated that sealed-off gas discharge tubes would have a short useful lifetime due to the discharge-caused dissociation of the gases, to counteract which he provides, inside the tubes, a carbon filament that, when heated by an electric current, is expected to regenerate the CO or $CO_2$ concentration level in the tube. Javan, on the other hand, solves the dissociation by continuously replenishing the gas in the non-sealed chamber by continuous flow of an unused gas mixture through the chamber via an inlet and an outlet tube. Both, Webley and Javan use internal electrodes which often shorten the useful life of the tubes.

It is one of the objects of the present invention to overcome the limitations and shortcomings of the prior-art IR gas analyzers, and to provide an infrared gas analyzer which is equipped with an IR-source that produces a noncontinuous spectrum comprising specific, discrete wavelengths only, selected to be essentially identical with the absorbable wavelengths forming the spectral "signature" of the target gas, is therefore highly specific, yields a very high signal to noise ratio compared to conventional BB-source equipped analyzers, has practically no thermal inertia and can therefore be modulated electronically rather than mechanically, has a sealed-off source with external electrodes, can be battery-operatable, and is compact, portable, highly selective and sensitive, yet very much cheaper than comparable prior-art IR-analyzers.

This the invention achieves by providing an infrared gas analyzer comprising:

a source of IR radiation containing at least one molecular, IR-active gas which, upon excitation, is capable of emitting IR radiation of a known, discrete spectral distribution;

a driver for providing energy for said excitation;

at least one detector placed at a distance from said source of IR radiation, which distance defines an analytical space wherein the gas to be analyzed is exposed to, and can absorb at least part of, said IR radiation, which detector serves for determining the absorption of said IR radiation by said gas in said space, and means responsive to the output of said detector, characterized in that said source of IR radiation is of the kind that produces a non-continuous spectrum comprising specific, discrete wavelengths only, being substantially those wavelengths that are characteristically absorbed by the gas the presence and concentration of which are to be established:

said gas is contained in a sealed-off enclosure;

said excitation is effected by electrical discharges taking place in a limited portion only of said sealed-off enclosure, the rest of said enclosure serving as a reservoir of said gas, and that electrodes producing said discharges are located outside of said enclosure.

The invention further provides an infrared gas analyzer comprising:

a source of IR radiation containing at least two IR-active gases, each of which, upon excitation, is capable of emitting IR radiation, the IR radiation of at least the second of said gases being of a known, discrete spectral distribution, a driver for providing energy for said excitation;

at least one detector placed at a distance from said source of IR radiation, which distance defines an analytical space wherein the gas to be analyzed is exposed to, and can absorb at least part of the IR radiation of said second gas, which detector serves for determining the absorption of said IR radiation by said gas in said space, and means responsive to the output of said detector, characterized in that the IR radiation of said second gas is of the kind that produces a non-continuous spectrum comprising specific, discrete wavelengths only, being substantially those wavelengths that are characteristically absorbed by the gas the presence and concentration of which is to be established;

said two gases are contained in a sealed-off enclosure subdivided by an IR-transparent partition wall into a first chamber containing at least said first gas and a second chamber containing at least said second gas;

said excitation is effected by electrical discharges taking place in a limited portion only of said first chamber, the rest thereof serving as reservoir of said first gas:

electrodes producing said discharges are located outside of said first chamber, and that said fragile, second gas in said chamber is excitable by IR radiation emitted from said first chamber through said partition wall.

A further drawback of all prior-art IR analyzers with BB-source resides in the fact that they are inherently incapable of detecting small shifts in absorbed wavelengths, as will occur when, for instance, an ordinary molecule is substituted by its rare isotope. Such capability can be achieved by using IR-sources with discrete emission spectra, in which the molecular gas in the source has been substituted by a chemically identical gas, but composed of molecules where at least one of its constituent atoms is replaced by its rare isotopes. The emission spectrum of such an isotope-substituted gas will show a slight shift as compared to that of molecules composed of the abundant isotopes, and will be absorbed mainly by molecules with the same rare isotope constitution, but not by the regular molecules. Typical cases are, e.g., the rare-isotope variants of regular $CO_2$, ($^{12}C^{16}O_2$) namely $^{13}C^{16}O_2$, $^{12}C^{18}O_2$, $^{12}C^{18}O^{16}O$, or the rare-isotope variants of regular $H_2O$: namely $D_2O$, HDO.

Being able to make use of such specific IR-sources, the IR-analyzer according to the invention is thus capable of identifying, and measuring the concentration of, isotopically substituted "marker" molecules.

It is also capable of producing from a single source two different, discriminable, specific radiations that, being chemically identical, will change identically with time, one of which radiations can be used as reference to the other to account for drifts in the system.

The invention will now be described in connection with certain preferred embodiments with reference to the following illustrative figures so that it may be more fully understood.

With specific reference now to the figures in detail, it is stressed that the particulars shown are by way of example and for purposes of illustrative discussion of the preferred embodiments of the present invention only and are presented in the cause of providing what is believed to be the most useful and readily understood description of the principles and conceptual aspects of the invention. In this regard, no attempt is made to show structural details of the invention in more detail than is necessary for a fundamental understanding of the invention, the description taken with the drawings making apparent to those skilled in the art how the several forms of the invention may be embodied in practice.

In the drawings:

FIG. 1 shows a block diagram of an IR-gas analyzer according to the present invention;

FIG. 2 is a graph comparing the discrete emission spectrum of an IR-SOURCE of the gas analyzer according to the invention with the continuous spectrum of the black-body radiator;

FIG. 3 is a schematic representation of a basic embodiment of the gas analyzer according to the invention;

FIG. 4 is another embodiment of the analyzer, comprising a reference cell, and

FIG. 5 is a schematic representation of yet another embodiment of the invention;

FIG. 6 is a schematic representation of an IR-source according to the invention;

FIG. 7 is a smaller representation of another embodiment of the source;

FIG. 8 schematically represents an embodiment of a source emitting test and reference signals, and FIG. 9 illustrates a composite source in which a fragile, IR-active gas is excited by optical pumping via a non-fragile gas.

Referring now to the drawings, there is seen in the block diagram of FIG. 1 a driver 2 powering and controlling an IR-source 4. The latter emits infrared radiation which passes through an analytical space 6 in which is located the gas to be analyzed. A detector 8 mounted downstream of the space 6 senses if and how much of the IR-radiation was absorbed by the gas. Signals from the detector 8 are amplified in the amplifier 10 and fed to the display unit 12 which indicates the concentration of the target gas in the analyzed sample.

The "heart" of the gas analyzer according to the invention is its IR-source which consists of a hermetically sealed-off vial or tube 4 containing a molecular, IR-active gas or a mixture of gases at, generally, subatmospheric pressure. When excited by electromagnetic waves in the RF (KHz, MHz) or microwave region, these vials act as electric discharge lamps, emitting IR radiation over a spectrum that, as already mentioned, is noncontinuous and consists of a band of discrete, well-defined lines. For every target gas, an IR-source is selected that will produce radiation of a spectrum substantially identical to the absorption band of that particular gas. In some cases, only the IR-active gas is introduced into the source vial 4. Others require additive gases that exhibit no roto-vibrational transitions, such as noble gases, or homonuclear diatomics such as $N_2$, $O_2$ or $H_2$ to enhance IR-emission and to reduce molecular dissociation due to the electrical discharge. The useful life of these IR-sources is at least several thousand hours of continuous operation.

The remarkable service life of these sources is achieved by several measures:

(1) Discharge takes place in a portion only of the vial 4, the rest of the vial serving as reservoir essential for maintaining proper gas composition in the discharge volume, which is several times smaller than the reservoir volume;

(2) Electrodes are disposed outside of the vial, and are therefore not liable to deterioration thus do not interfere with the critical purity of the gas contents. Also, sputtering of the electrode and its deposition on the transparent walls of the gas enclosure are stopped. Excitation is effected either by capacitive, inductive or radiative coupling. The electrodes are in the first case flat metal rings, or parts of such rings, surrounding the vial 4, preferably contacting the vial surface and, in the second case, wire coils analogously positioned.

The IR-active molecular gases as well as the atomic or molecular buffer gases are maintained at pressures not exceeding several tenths of a Torr for low-power excitation.

In some cases it is advantageous to provide the IR-source with spectral filters consisting of absorption cells filled with a gas the specific absorbable radiation of which is involuntarily emitted from the discharge zone due to the presence, in this zone, of IR-active molecules or radicals different from those of the target gas.

Similar absorbing means can also be provided for when the presence is likely, in the tested gas mixture, of a certain gas with an absorption band liable to be superposed upon the target gas band.

The vials can be made of any suitable material, but must have at least one region, serving as outlet "window", capable of transmitting an amount of radiation specific to the target gas, significant enough to permit detection of the radiation and of its absorption. Different target gases will make necessary the choice of different window materials, e.g. soda glass, pyrex, sapphire, barium fluoride, etc. A source can be provided for emitting radiation for more than one gas with filters used to select a given radiation at a given time.

The power required to drive these IR-tubes is exceedingly small, varying from fractions of a watt to a few watts and, for a given emitted power level of the relevant radiation absorbed by the target gas, is lower by up to two orders of magnitude than that required for conventional BB-radiators.

In FIG. 2 the narrow, distinct and discrete line spectrum A of the IR-source of the analyzer according to the invention is compared with the broad, continuous spectrum B of a BB-radiator at 1200° C. The A-spectrum shown matches the $CO_2$ absorption band.

A basic embodiment of the IR-gas analyzer according to the invention is illustrated in FIG. 3. There is seen the driver 2, which comprises a power source 14, a modulator 16 which serves as an electronic "chopper" producing, e.g., a square-wave like pulse of selectable duty cycle and rate, and an oscillator 18 acting as an RF source. The IR-tube 4 is capacitatively coupled to the RF-source 18 by means of metal rings 20 which serve a capacitor plates, and a coaxial cable 22. Optical means can be used to direct the radiation into the analytical cell.

The analytical cell 6 has an inlet 24 and an outlet 26, as well as two windows 28 which, obviously, must be at least partially transparent to the specific IR-radiation emitted by the source 4.

For many applications, however, the gas sample need not be confined in a cell. With the IR-radiation suitably concentrated or collimated by optical means per se known, measurements can be taken also in free space over relatively large distances intervening between the source 4 and the detector 8. It is thus possible to measure or monitor CO levels in vehicular tunnels, or in chimneys, or the like.

The IR-detector 8 is of the commercially available type, e.g., a lead selenide detector such as OE-15-54 manufactured by Optoelectronics. It could also be an Eltec 408 pyroelectric type detector, or a photoacoustic detector. A detector working on a different principle consists of a cell having an IR-permeable window and filled with an IR-absorbing gas which, in dependence of the amount of radiation absorbed, heats up, temperature variations being measured with the aid of a thermocouple.

In some cases the detector is arranged to process test and reference signals in sequence, at different and specific times, switching over being effected by an "information" link between the IR-source and the detector.

The output of the detector 8 is processed and amplified in the amplifier 10 and eventually reaches the display unit 12. The latter can have many forms, analog or digital, giving the concentration in %, ppm, etc. Where absolute values or great accuracy are not required, concentrations may be indicated by a number of LED's, with more LED's lighting up the higher the concentration determined. Other indicating means may include optical or acoustical or speech warning devices.

FIG. 4 schematically illustrates a further embodiment, in which use is made of a reference cell 6', filled with a known concentration of the target gas, say $CO_2$ or with a "transparent" solid or gas like $N_2$, and having its own detector 8'. The outputs from the two detectors 8 and 8' are fed to an electronic unit 30, where they are compared and the thus processed signal amplified and transmitted to the display unit 12 and/or to a control unit 13 used for controlling equipment such as blowers, exhausters, humidifiers, etc., to maintain target-gas concentrations within presettable limits.

Yet another embodiment is illustrated in the schematic drawing of FIG. 5. A gas analyzer of this type is used for clinical purposes in the determination of the $CO_2$-content of exhalation air. The patient inhales and exhales through the tubular cell 6 which, during the inhalation stroke I, acts as reference cell, passing as it does the room air with its known $CO_2$ content. During the exhalation stroke E, $CO_2$ concentration in the tubular cell 6—now acting as analytical cell—increases, causing absorption to increase, and the detector will consequently receive less radiation. Detector signals after each stroke are compared in the comparator and amplifier unit 30, and the exhalation value fed to the display unit 12.

FIG. 6 represents an IR-source according to the invention. There is seen the vial 4, the electrodes 20 which in this embodiment consist of rings of metal foil attached to the vial and connected to the driver 2 (FIG. 1) by means of a coaxial cable 22. While in this embodiment the vial 4 is capacitively coupled with the RF-source, inductive coupling is also possible, as has already been mentioned, by replacing the two electrodes 20 by a wire coil.

Electrical discharge takes place only in the zone 32 delimited by the electrodes 20, the rest of the vial volume serving as reservoir 34 used to maintain the proper gas composition of the discharge zone 32. In many applications, the IR-radiation would be emitted in direction of arrow A. However, by appropriate choise of window material vs. envelope material, radiation can also be emitted in direction of arrow B.

FIG. 7 schematically represents another embodiment, in which the IR-radiation is emitted over a relatively wide front, as indicated by the arrows. Here, the extent, in depth, of the discharge zone 32 is defined by the circumferential reach of the electrodes 20. The vial volume below that reach constitutes the reservoir 34.

FIG. 8 shows an embodiment of the IR-source that simultaneously emits test as well as reference signals. The vial 4 in this embodiment is U-shaped, each limb of the U having a set of electrodes 20 and a window 36. The gas filling of the vial is such as to produce two different radiations, one of which is the test radiation T which is to be absorbed by the target gas, the other is the reference radiation R, which is not absorbed by the gas. Further provided are two filters 38, 40, the first one of which filters out the test radiation T, leaving only the reference radiation R, the other one filtering out the reference radiation R, leaving only the test radiation T. The relative intensities of T and R are at a known and fixed ratio that will not change with time, even if vial output should vary due to aging, surges, or the like. The vial is connected to a driver which alternatingly excites one pair of electrodes 20 at a time, and so the source alternatingly emits radiations of different spectral composition from different portions of the source.

The embodiment shown in FIG. 9 provides a solution to the problem of molecular gases P which are fragmented in the presence of energetic electrons such as those prevailing in an electrical discharge and for which the embodiments discussed so far do not provide a satisfactory rate of recombination.

As can be seen in FIG. 9, the vial 4 is subdivided by an IR-transparent partition wall 4 into two chambers, a first chamber 44 and a second chamber 46. Chamber 44 acts like any of the sources described above which contain an IR-active gas A, and chamber 46 contains a mixture of at least the gases A and P in an appropriate ratio.

Resonant IR-radiation emitted by gas A from chamber 44 into chamber 46 is absorbed by the gas component A in chamber 46, producing excited vibrational states of molecules A. By v—v transfer, energy is transferred from molecules A to molecules P, which now radiate their specific IR-radiation when decaying to the ground state. This type of activation is known as optical pumping.

To have an efficient v—v transfer between A and P, A has to be chosen so as to have a close energy match with the relevant energy levels of P.

It will be evident to those skilled in the art that the invention is not limited to the details of the foregoing illustrative embodiments and that the present invention may be embodied in other specific forms without departing from the spirit or essential attributes thereof. The present embodiments are therefore to be considered in all respects as illustrative and not restrictive, the scope of the invention being indicated by the appended claims rather than by the foregoing description, and all changes which come within the meaning and range of equivalency of the claims are therefore intended to be embraced therein.

What is claimed is:

1. An infrared gas analyzer comprising:
    a source of IR radiation containing at least one molecular, IR-active gas which, upon excitation, emits IR radiation of a known, discrete spectral distribution;
    driver means for providing energy for said excitation;
    at least one detector placed at a distance from said source of IR radiation, which distance defines an analytical space wherein a gas to be analyzed is exposed to, and absorbs at least part of, said IR radiation, which at least one detector serves for determining the absorption of said IR radiation by said gas to be analyzed, and
    means responsive to the output of said at least one detector,
    characterized in that said source of IR radiation is of the kind that produces a non-continuous spectrum comprising specific, discrete wavelengths only, being substantially those wavelengths that are characteristically absorbed by the gas the presence and concentration of which are to be established;
    said IR-active gas is contained in a sealed-off enclosure;
    means for effecting said excitation are electrical discharges taking place in a limited portion only of said sealed-off enclosure, the rest of said enclosure serving as a substantially non-excited reservoir of said IR-active gas, and
    that means for producing said discharges comprise electrodes located outside of said enclosure.

2. The gas analyzer as claimed in claim 1, wherein said analytical space is an analyzing cell accessible to the gas to be analyzed, said cell being located between said IR-source and said at least one detector, and having at least an inlet window and an outlet window that are substantially transparent to the radiation emitted by said IR-source.

3. The gas analyzer as claimed in claim 1, wherein said analytical space is a tubular duct carrying alternatingly the gas to be analyzed and a reference gas, and having at least an inlet window and an outlet window substantially transparent to the radiation emitted by said IR-source.

4. The gas analyzer as claimed in claim 1, further comprising a closed reference cell containing a known gas of a known concentration, and having at least an inlet window and an outlet window substantially transparent to the radiation emitted by said IR-source.

5. The gas analyzer as claimed in claim 4, further comprising a second detector, located downstream of said reference cell.

6. The gas analyzer as claimed in claim 1, wherein said driver means comprises a source of electrical power, a modulator and an oscillator.

7. The gas analyzer as claimed in claim 1, wherein said responsive means is a display unit.

8. The gas analyzer as claimed in claim 4, wherein said responsive means is a control unit for controlling equipment for maintaining said concentration within presettable limits.

9. The gas analyzer as claimed in claim 1, wherein said source of IR-radiation produces at least two different radiations, one radiation being a test radiation to be absorbed by the gas to be analyzed, the other being a reference radiation nonabsorbable by said gas to be analyzed, further comprising filter means to filter out, from said two different radiations, at least said test radiation to produce a beam of reference radiation.

10. An infrared gas analyzer comprising:
    a source of IR radiation containing at least two IR-active gases, a first and a second gas, each of which, upon excitation, emits IR radiation, the IR radiation of at least the second of said gases being of a known, discrete spectral distribution,
    driver means for providing energy for said excitation;
    at least one detector placed at a distance from said source of IR radiation, which distance defines an analytical space wherein a gas to be analyzed is exposed to, and absorbs at least part of the IR radiation of said second gas, which at least one detector serves for determining the absorption of said IR radiation by said gas to be analyzed, and
    means responsive to the output of said at least one detector,
    characterized in that the IR radiation of said second gas is of the kind that produces a non-continuous spectrum comprising specific, discrete wavelengths only, being substantially those wavelengths that are characteristically absorbed by the gas the presence and concentration of which is to be established;
    said two IR-active gases are contained in a sealed-off enclosure subdivided by an IR-transparent partition wall into a first chamber containing at least said first gas and a second chamber containing at least said second gas;
    means for effecting said excitation are electrical discharges taking place in a limited portion only of said first chamber, the rest thereof serving as a substantially non-excited reservoir of said first gas;
    means for producing said discharges comprise electrodes located outside of said first chamber, and that said, second gas in said second chamber is excitable by IR radiation emitted from said first chamber through said partition wall.

11. A source of IR radiation for use with an infrared gas analyzer, characterized in that:

said source comprises a sealed-off enclosure containing at least one molecular, IR-active gas which, upon excitation, emits IR-radiation of a known, discrete spectral distribution;

means for effecting said excitation are electrical discharges taking place in a limited portion only of said sealed-off enclosure, the rest of said enclosure serving as a substantially non-excited reservoir for said gas, and that means for producing said discharges are electrodes disposed outside of said enclosure.

12. A source of IR radiation for use with an infrared gas analyzer, characterized in that:

said source comprises a sealed-off enclosure subdivided by an IR-transparent partition wall into a first chamber containing at least a first, molecular, IR-active gas, and a second chamber containing at least a second, molecular, IR-active gas, which first gas, upon excitation, emits IR radiation penetrating said partition wall and causing said second gas to become excited and to emit an IR radiation of a known, discrete spectral distribution;

means for effecting excitation of said first gas are electrical discharges in a limited portion only of said first chamber, the rest thereof serving as a substantially non-excited reservoir of said first gas, and that means for producing said discharges comprise electrodes disposed outside of said enclosure.

* * * * *